(12) United States Patent
Mongeon et al.

(10) Patent No.: US 7,561,913 B2
(45) Date of Patent: Jul. 14, 2009

(54) AUTOMATIC ADJUSTING R-WAVE SYNCHRONIZATION ALGORITHM FOR ATRIAL CARDIOVERSION AND DEFIBRILLATION

(75) Inventors: Luc R. Mongeon, Minneapolis, MN (US); Rahul Mehra, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 687 days.

(21) Appl. No.: 10/426,284

(22) Filed: Apr. 30, 2003

(65) Prior Publication Data

US 2004/0220630 A1    Nov. 4, 2004

(51) Int. Cl.
*A61N 1/39* (2006.01)

(52) U.S. Cl. ......................................... 607/5

(58) Field of Classification Search ............... 607/4–15, 607/25
See application file for complete search history.

(56) References Cited

U.S. PATENT DOCUMENTS

| | | | |
|---|---|---|---|
| 3,952,750 A | 4/1976 | Mirowski et al. | |
| 4,375,817 A | 3/1983 | Engle et al. | |
| 4,384,585 A | 5/1983 | Zipes | |
| 4,577,633 A | 3/1986 | Berkovits et al. | |
| 4,587,970 A | 5/1986 | Holley et al. | |
| 4,726,380 A | 2/1988 | Vollmann et al. | |
| 4,830,006 A | 5/1989 | Haluska et al. | |
| 4,880,005 A | 11/1989 | Pless et al. | |
| 4,949,719 A | 8/1990 | Pless et al. | |
| 5,107,850 A | 4/1992 | Olive | |
| 5,117,824 A | 6/1992 | Keimel et al. | |
| 5,161,527 A | 11/1992 | Nappholz et al. | |
| 5,188,105 A | 2/1993 | Keimel | |
| 5,207,219 A | 5/1993 | Adams et al. | |
| 5,411,524 A | 5/1995 | Rahul | |
| 5,545,186 A | 8/1996 | Olson et al. | |
| 5,560,369 A | 10/1996 | McClure et al. | |
| 5,620,471 A | 4/1997 | Duncan | |
| 5,720,295 A | 2/1998 | Greenhut et al. | |
| 5,755,736 A | 5/1998 | Gillberg et al. | |
| 5,755,737 A | 5/1998 | Prieve et al. | |
| 5,776,164 A | 7/1998 | Ripart | |
| 5,792,202 A * | 8/1998 | Rueter ..................... 607/27 |
| 5,843,130 A | 12/1998 | Jazayeri | |
| 5,853,426 A * | 12/1998 | Shieh ....................... 607/5 |
| 5,999,850 A * | 12/1999 | Dawson et al. ............ 607/4 |

(Continued)

FOREIGN PATENT DOCUMENTS

WO    WO 95/28987 A1    11/1995

(Continued)

*Primary Examiner*—Angela D Sykes
*Assistant Examiner*—Michael Kahelin
(74) *Attorney, Agent, or Firm*—Michael C. Soldner (57) ABSTRACT

An implantable medical device system and method are provided for synchronizing atrial cardioversion shocks to the ventricular rhythm using an adjustable atrial cardioversion/defibrillation ventricular refractory period. Upon determining a need for an atrial shock therapy, the method determines if the ventricular rate meets synchronization criteria based on an upper ventricular refractory period limit. If synchronization criteria are not met, the refractory period is automatically adjusted in stepwise decrements until the synchronization criteria are met, or until a lower refractory period limit is exceeded. If synchronization criteria are met, an atrial shock is synchronized to the next ventricular depolarization occurring outside the current refractory period. If the lower refractory period limit is exceeded, the atrial therapy is aborted.

17 Claims, 5 Drawing Sheets

U.S. PATENT DOCUMENTS

| | | | |
|---|---|---|---|
| 6,081,745 A | 6/2000 | Mehra | |
| 6,122,546 A | 9/2000 | Sholder et al. | 607/9 |
| 6,430,438 B1 * | 8/2002 | Chen et al. | 607/5 |
| 6,625,490 B1 * | 9/2003 | McClure et al. | 607/9 |
| 6,963,776 B2 * | 11/2005 | Seim | 607/14 |
| 2002/0147471 A1 | 10/2002 | Seim | 607/14 |
| 2003/0135242 A1 | 7/2003 | Mongeon et al. | 607/5 |

FOREIGN PATENT DOCUMENTS

WO     WO 95/28988 A1     11/1995

\* cited by examiner

AUTOMATIC ADJUSTING R-WAVE SYNCHRONIZATION ALGORITHM FOR ATRIAL CARDIOVERSION AND DEFIBRILLATION

FIELD OF THE INVENTION

The present invention relates generally to the field of implantable electrical medical devices and more specifically to an implantable medical device and method for controlling the delivery of R-wave synchronized atrial cardioversion or defibrillation shocks.

BACKGROUND OF THE INVENTION

In the past, atrial arrhythmias have been largely undertreated due to the perception that these arrhythmias are relatively benign. As more serious consequences of persistent atrial fibrillation have come to be understood, such as an associated risk of relatively more serious ventricular arrhythmias and stroke, there is a greater interest in providing implantable atrial or dual chamber cardioverter defibrillators for treating atrial arrhythmias. In such devices, it is desirable to synchronize delivery of a high-energy atrial cardioversion or defibrillation pulse, referred to herein as a "shock", to a ventricle depolarization to avoid inducing ventricular arrhythmias due to stimulation during the ventricular vulnerable period.

A number of proposals have been set forth for controlling the timing of atrial cardioversion and defibrillation shocks. An early disclosure of an implantable atrial defibrillator, U.S. Pat. No. 3,952,750 issued to Mirowski et al., proposes synchronizing delivery of the atrial defibrillation pulse to a sensed R-wave. However, because cardioversion or defibrillation shocks synchronized to a ventricular rhythm that is too rapid or unstable may induce ventricular arrhythmias, more complex systems have been proposed for controlling the synchronization of atrial cardioversion with the ventricular rhythm. For example, as proposed in U.S. Pat. No. 5,207,219, issued to Adams et al., atrial defibrillation shocks are delivered synchronized to sensed ventricular depolarizations only when the ventricular depolarizations follow preceding ventricular depolarizations by an interval greater than a minimum V-V interval. In U.S. Pat. No. 5,843,130 issued to Jazayeri, a system for providing delivery of an atrial defibrillation shock synchronized only to beats during heart rate deceleration is proposed.

An implantable atrial defibrillator that applies an atrial therapy only if the ventricle is stable to insure that the therapy does not provoke a ventricular tachycardia is generally disclosed in U.S. Pat. No. 5,999,850, issued to Dawson et al. A cardiac rhythm management system that includes atrial shock timing optimization and actively stabilizes the ventricular heart rate to obtain less potentially proarrhythmic conditions is generally disclosed in U.S. Pat. No. 6,430,438 issued to Chen et al.

Commercially available ICDs typically include some method to assure that a minimum R-R interval has elapsed as a pre-requisite to delivering an atrial shock. One such method for synchronizing atrial defibrillation to a ventricular rhythm that is not too fast requires a ventricular depolarization to fall outside a defined refractory period following the immediately preceding ventricular depolarization, as in the Medtronic, Inc. Jewel® AF, Model 7250 Implantable Cardioverter Defibrillator. This method ensures that atrial defibrillation will safely be synchronized to a ventricular rate that is not too fast. However, one limitation of setting a fixed refractory period is that, if the ventricular rate is just slightly faster than the fixed refractory period, an atrial cardioversion or defibrillation therapy will not be delivered, even though the ventricular rate may be stable and a synchronized atrial therapy could be safely delivered.

Another clinical limitation of this safety feature has arisen when patient's equipped with a patient programmer attempt to initiate an atrial defibrillation therapy. If the ventricular rate is faster than the corresponding programmed refractory period required to synchronize atrial defibrillation, the atrial defibrillation that the patient is expecting will not occur, giving the patient the perception that the device is malfunctioning.

It is desirable therefore, to provide an improved method for synchronizing atrial cardioversion or defibrillation therapies to a ventricular rhythm, which allows ventricular synchronized atrial shock delivery when the ventricular rate is near the programmed limit but does not quite reach a fixed rate limit for synchronization.

SUMMARY OF THE INVENTION

The present invention provides an implantable cardioverter defibrillator system and method for synchronizing atrial cardioversion shocks to the ventricular rhythm using an adjustable atrial cardioversion/defibrillation ventricular refractory period. Employing an adjustable refractory period allows ventricular synchronization of an atrial shock to occur up to a variable maximum ventricular rate limit.

The system includes an ICD and associated set of leads, wherein the ICD is capable of sensing atrial and ventricular rhythms and delivering high-voltage atrial cardioversion or defibrillation shocks synchronized to a sensed ventricular depolarization. When the ICD determines that atrial cardioversion or defibrillation is needed, the ICD employs a synchronization method according to the present invention for controlling the atrial shock delivery.

The synchronization method of the present invention attempts to synchronize the atrial cardioversion shock to a ventricular depolarization after programmed criteria required for synchronization are met. Synchronization criteria typically include a predetermined number of R-R intervals that must fall outside an atrial cardioversion/defibrillation ventricular refractory period. If the synchronization criteria are not satisfied, the atrial cardioversion/defibrillation ventricular refractory period is automatically adjusted by a predetermined decrement. The refractory period continues to be adjusted in stepwise decrements until a lower refractory period limit is reached or until synchronization criteria are met, which ever occurs first. If the lower refractory period limit is reached first, the atrial therapy is aborted. If synchronization criteria are met at an adjusted refractory period, an atrial cardioversion or defibrillation shock is synchronized to the next ventricular depolarization falling outside the adjusted refractory period. In one embodiment of the present invention, synchronization criteria further include verification of a stable ventricular rate.

DETAILED DESCRIPTION OF THE INVENTION

Figure 1:
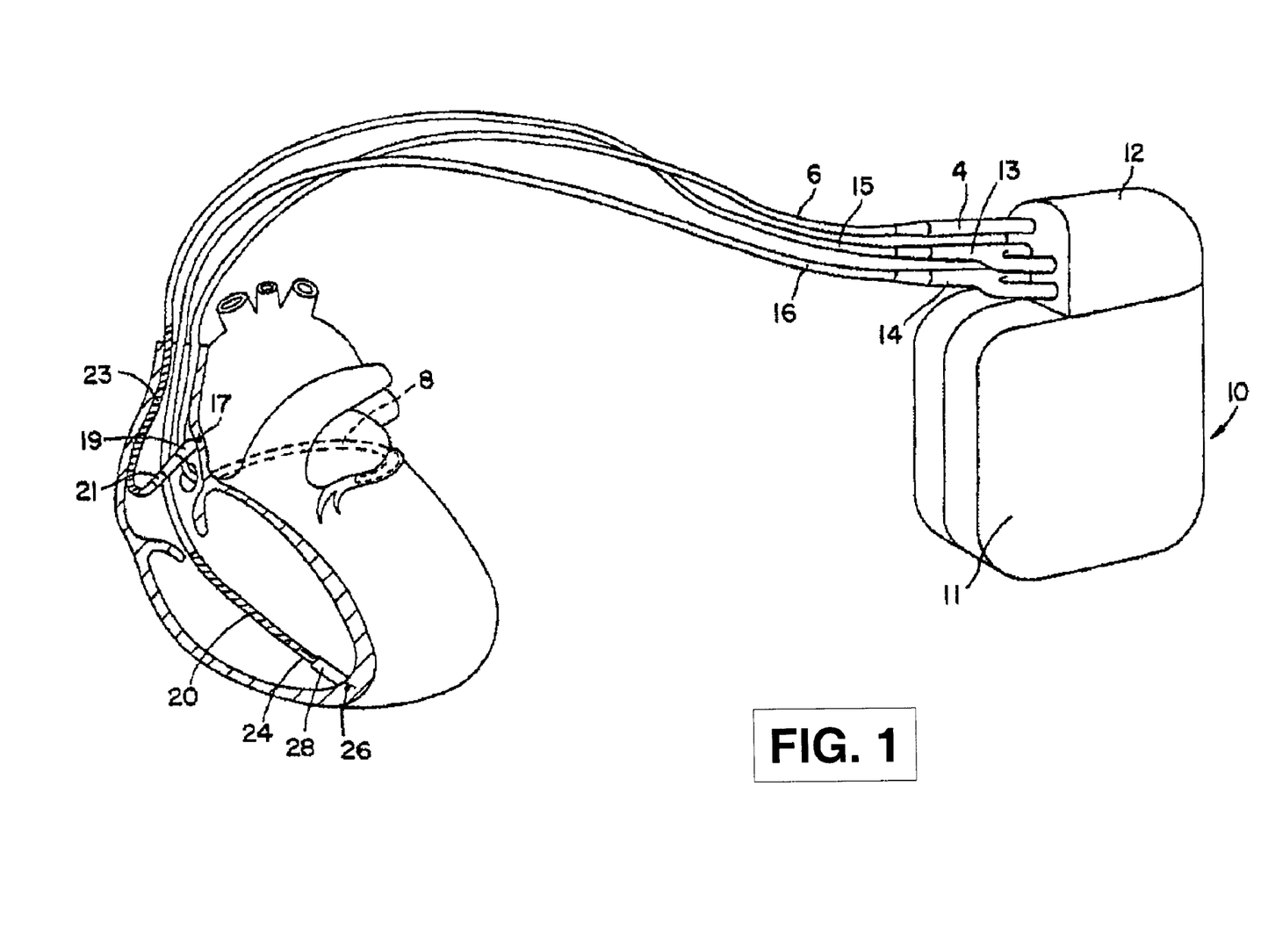
FIG. 1 is an illustration of an exemplary implantable pacemaker cardioverter defibrillator (ICD) system in which the present invention may be practiced.

FIG. 1 is an illustration of an exemplary implantable pacemaker cardioverter defibrillator (ICD) system in which the present invention may be practiced. ICD 10 is coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers.

In FIG. 1, the right ventricular lead 16 is positioned such that its distal end is in the right ventricle (RV) for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and RV coil electrode 20, each of which are connected to an insulated conductor contained within the body of lead 16. The proximal end of the insulated conductors are coupled to corresponding connectors carried by bifurcated connector 14 at the proximal end of lead 16 for providing electrical connection to the ICD 10.

The right atrial lead 15 is positioned such that its distal end is in the vicinity of the right atrium and the superior vena cava (SVC). Lead 15 is equipped with a ring electrode 21 and an extendable helix electrode 17, mounted retractably within electrode head 19, for sensing and pacing in the right atrium. Lead 15 is further equipped with an SVC coil electrode 23 for delivering high-energy shock therapy. The ring electrode 21, the helix electrode 17 and the SVC coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the RV coil electrode 20 or the SVC coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may be adapted for use with other atrial, dual chamber, or multichamber ICD systems.

Figure 2:
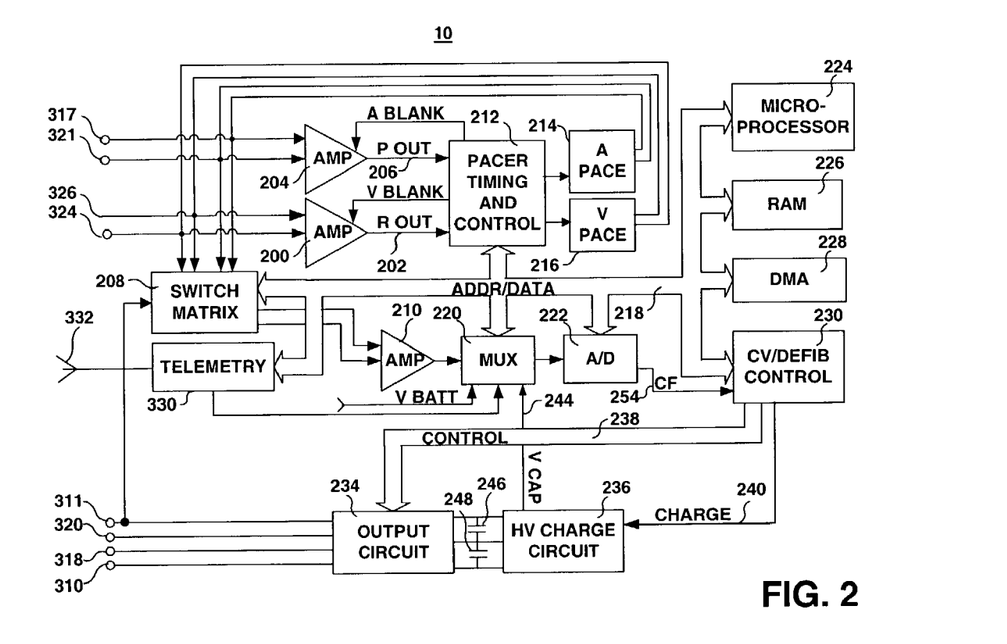
FIG. 2 is a functional block diagram of an ICD in which the present invention may usefully be practiced.

FIG. 2 is a functional block diagram of an ICD in which the present invention may usefully be practiced. This diagram should be taken as exemplary of the type of device with which the invention may be embodied and not as limiting, as it is believed that the invention may usefully be practiced in a wide variety of device implementations, including devices providing therapies for treating only atrial arrhythmias, devices which do not provide anti-tachycardia pacing therapies or devices that do not include bradycardia pacing. The disclosed embodiment shown in FIG. 2 is a microprocessor-controlled device, but the methods of the present invention may also be practiced with devices employing dedicated digital circuitry for controlling some device functions.

With regard to the electrode system illustrated in FIG. 1, the ICD 10 is provided with a number of connection terminals for achieving electrical connection to the cardiac leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methods known in the art.

The telemetry circuit 330 receives downlink telemetry from and sends uplink telemetry to an external programmer, as is conventional in implantable anti-arrhythmia devices, by means of an antenna 332. Received telemetry is provided to microprocessor 224 via multiplexer 220. Data to be uplinked to the programmer and control signals for the telemetry circuit 330 are provided by microprocessor 224 via address/data bus 218. Numerous types of telemetry systems known for use in implantable devices may be used.

The remainder of circuitry illustrated in FIG. 2 is dedicated to the provision of cardiac pacing, cardioversion and defibrillation therapies and, for the purposes of the present invention, may correspond to circuitry known in the prior art. In the exemplary embodiment shown in FIG. 2, the pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals, P-P intervals, P-R intervals, and R-P intervals, which measures are stored in memory 226 and used to diagnose the occurrence of a variety of arrhythmias.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/control circuitry 212 take place following such interrupts. A portion of the random access memory 226 may be configured as a number of recirculating buffers capable of holding a series of measured intervals, which may be analyzed in response to a pace or sense interrupt by microprocessor 224 for diagnosing an arrhythmia.

The present invention may employ any arrhythmia detection algorithm known in the art to detect the occurrence of arrhythmias. For example, the detection methods disclosed in U.S. Pat. No. 5,545,186 issued to Olson et al., and in U.S. Pat. No. 5,755,736 issued to Gillberg et al., both patents incorporated herein by reference in their entirety, for the detection of atrial fibrillation and tachycardias may be employed. Alternatively, other known detection algorithms for use in conjunction with ICDs such as those disclosed in U.S. Pat. No. 5,161,527 issued to Nappholz et al, U.S. Pat. No. 5,720,295 issued to Greenhut et al., or U.S. Pat. No. 5,107,850 issued to Olive, all incorporated by reference in their entireties may also be employed.

A device embodying the present invention may also include the ability to treat ventricular tachyarrhythmias, as discussed above. In the event such capability is desired, any of the prior art ventricular tachyarrhythmia detection methods may be employed, including those in the above cited Olson patent and Gillberg et al. patent, as well as the detection methods disclosed in U.S. Pat. No. 5,620,471 issued to Duncan, U.S. Pat. No. 4,880,005 issued to Pless et al., and U.S. Pat. No. 5,560,369 issued to McClure et al., all incorporated by reference in their entireties as well.

In addition, the device may be configured such that the patient initiates delivery of the therapy by means of an external controller, such that the device may not employ a detection method of its own as a prerequisite to a delivery of therapy. In this context, a patient activator as disclosed in U.S. Pat. No. 5,755,737, issued to Prieve et al, incorporated by reference in its entirety herein, may be employed. The particular choice of patient activator is not critical to the success of the invention, and any workable method for initiating the delivery of the atrial cardioversion or defibrillation therapy may usefully be employed.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in the above-cited U.S. Pat. No. 4,880,005, issued to Pless et al. and in U.S. Pat. No. 4,577,633, issued to Berkovits et al., U.S. Pat. No. 4,726,380, issued to Vollmann et al., and U.S. Pat. No. 4,587,970, issued to Holley et al., all of which are incorporated herein by reference in their entireties may also be used.

In the event that generation of a cardioversion or defibrillation pulse is required, microprocessor 224 employs the escape interval counter to control timing of such cardioversion and defibrillation shocks, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212.

One embodiment of an appropriate system for delivery and synchronization of ventricular cardioversion and defibrillation shocks and for controlling the timing functions related to them is disclosed in more detail in commonly assigned U.S. Pat. No. 5,188,105 by Keimel, incorporated herein by reference in its entirety. Any known ventricular cardioversion or defibrillation pulse control circuitry is believed usable in conjunction with the present invention. For example, circuitry controlling the timing and generation of cardioversion and defibrillation shocks as disclosed in U.S. Pat. No. 4,384,585, issued to Zipes on May 24, 1983, in U.S. Pat. No. 4,949,719 issued to Pless et al, and in U.S. Pat. No. 4,375,817, issued to Engle et al, all incorporated herein by reference in their entireties may also be employed. In addition, high frequency pulse bursts may be delivered to electrode terminals 317 and 321 to terminate atrial tachyarrhythmias, as described in PCT Patent Publication No. WO95/28987, filed by Combs et al., and PCT Patent Publication No. WO95/28988, filed by Mongeon et al, both incorporated herein by reference in their entireties.

In the illustrated device, delivery of cardioversion or defibrillation shocks is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachycardia pacing may be undertaken prior to delivery of cardioversion shocks if the rate of the detected tachycardia is above a preset threshold. The references cited above in conjunction with descriptions of prior art tachycardia detection and treatment therapies are applicable here as well.

In the event that atrial fibrillation is identified, high frequency burst stimulation as discussed above may be employed as the initial attempted therapy. Subsequent therapies may be delivery of high amplitude defibrillation shocks, typically in excess of 5 joules. Lower energy levels may be employed for cardioversion. As in the case of currently available ICDs, and as discussed in the above-cited references, it is envisioned that the amplitude of the defibrillation shock may be incremented in response to failure of an initial shock or shocks to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,726,380, issued to Vollmann et al. and U.S. Pat. No. 4,587,970, issued to Holley et al.

Figure 3:
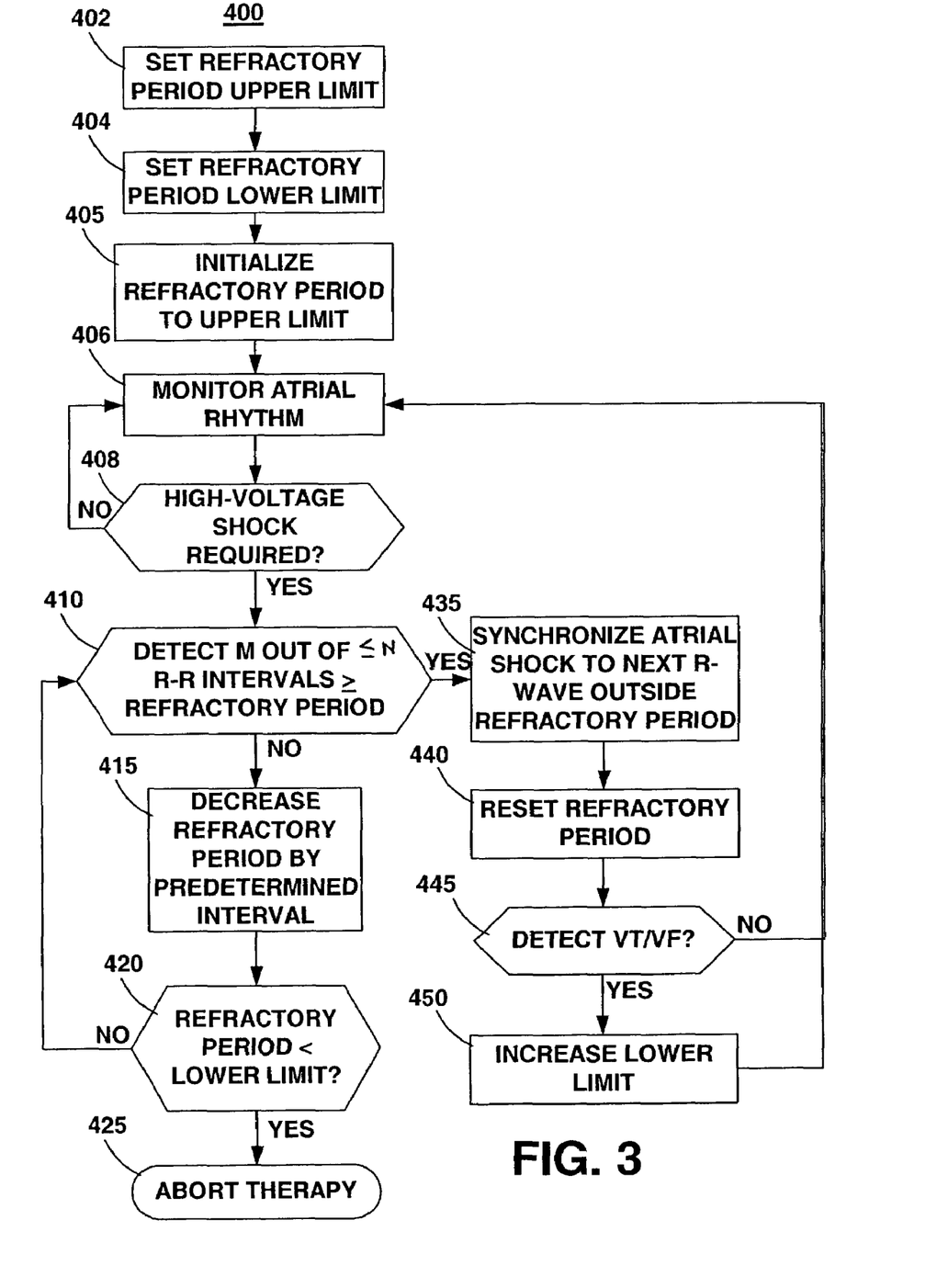
FIG. 3 is a flow chart of a method for controlling the synchronization of an atrial defibrillation or cardioversion shock with a ventricular depolarization, according to the present invention.

FIG. 3 is a flow chart of a method for controlling the synchronization of an atrial defibrillation or cardioversion shock with a ventricular depolarization, according to the present invention. A synchronization method employed according to the present invention for synchronizing atrial high-voltage cardioversion or defibrillation therapy utilizes an upper refractory period limit and a lower refractory period limit in determining if the atrial therapy can be safely synchronized to the ventricular rate, rather than a single fixed refractory period as used on prior art. As such, prior to executing the synchronization method, the upper and lower refractory period limits are set at step 402 and 404, respectively. These parameters are preferably programmable and may be initially set to nominal settings which can be reprogrammed by a clinician at the time of device implant or at any time after implant. A typical upper refractory period limit is 500 ms, corresponding to a ventricular rate of 120 beats per minute. A typical lower refractory period limit may be 400 ms, corresponding to a ventricular rate of 150 beats per minute. The programmable settings available in a particular device may be constrained within a fixed range to prevent programming of an extremely long upper limit that would generally be considered too limiting in synchronizing atrial cardioversion/defibrillation or an extremely short lower limit that would generally be considered unsafe under all conditions for ventricular synchronization of atrial cardioversion/defibrillation. Alternatively, upper and lower refractory limits may be set as fixed parameters within the device.

At step 405, the operating atrial cardioversion/defibrillation ventricular refractory period is initialized to the programmed (or fixed) upper limit. By initially setting the refractory period to the upper limit, synchronization of atrial cardioversion/defibrillation therapies will first be attempted at the corresponding, relatively lower, ventricular rate before attempting synchronization of atrial shocks at higher ventricular rates, as will be described in greater detail below.

Step 406 represents the normal device operation performed for detecting an atrial arrhythmia, according to any of the arrhythmia detection methods described or referenced above. Based on the monitored cardiac rhythms, a determination is made as to whether delivery of a high-voltage cardioversion or defibrillation shock is needed, indicated at step 408. The need for an atrial cardioversion or defibrillation shock may arise due to automatic atrial arrhythmia detection by the ICD or in response to a patient-initiated therapy. It is recognized that detection of an atrial arrhythmia during atrial rhythm monitoring at step 406 may initiate a menu of tiered therapies, which may result in successful termination of the atrial arrhythmia prior to requiring a cardioversion/defibrillation shock.

After determining that a cardioversion/defibrillation shock is needed, the ventricular rhythm is monitored at decision step 410 to determine if synchronization criteria are met for delivering the atrial shock. In one embodiment, synchronization criteria require that the device detect a certain number M out f less than N RR intervals meet or exceed the current atrial synchronization ventricular refractory period. Typically a minimum of 2 R-R intervals longer than the refractory period out of 12 or less consecutive R-R intervals are required for satisfying the criteria for delivering an atrial cardioversion/defibrillation shock synchronized to a ventricular depolarization. It is recognized, however, that the number of required intervals exceeding the refractory period may be set according to any desired alternative criteria. It is further recognized that synchronization criteria may be defined according to alternative requirements such as requiring a given number of consecutive R-R intervals greater than the refractory period.

If the synchronization criteria are met at step 410, a cardioversion/defibrillation shock is delivered to the atrium, synchronized with the next R-wave that falls outside the ventricular refractory period. If, however, the synchronization requirements are not met at step 410, the atrial cardioversion/defibrillation ventricular refractory period is automatically adjusted by a predetermined decrement at step 415. For example, the refractory period may be decreased by an interval on the order of 10 to 20 ms. At decision step 420, the adjusted refractory period is compared to the lower refractory period limit. If the adjusted refractory period is less than the lower limit, the atrial cardioversion/defibrillation therapy is aborted at termination step 425.

If the adjusted refractory period is not less than the lower limit, the process returns to step 410 to determine if the synchronization criteria are now met according to the adjusted refractory period. If not, steps 415 and 420 are repeated until the synchronization criteria are satisfied at decision step 410 or until the lower refractory period limit is exceeded, as determined at decision step 420.

If the synchronization criteria are satisfied at an adjusted refractory period (step 410), the atrial therapy is delivered at step 435, synchronized to the next R-wave falling outside the adjusted ventricular refractory period. At step 440, the refractory period is preferably reset to the upper refractory period limit, such that subsequent atrial therapy synchronization attempts will be performed beginning at the upper refractory limit, associated with a slower ventricular rate.

At decision step 445, method 400 continues to monitor the ventricular rhythm to determine if the synchronized atrial shock induces a ventricular arrhythmia. If ventricular tachycardia (VT) or ventricular fibrillation (VF) is detected within a specified period of time after the synchronized atrial shock, the lower refractory period limit is preferably reset at step 450 to some interval greater than the current operating refractory period, such as the previous refractory period, or the upper limit, for example, so that subsequent atrial therapy synchronization attempts are not repeated at the current operating refractory period which has resulted in VT or VF.

Method 400 then returns to step 406 and continues monitoring the atrial rhythm. If detection of the atrial arrhythmia continues due to failure of the delivered shock to cardiovert or defibrillate the atrium, or if a new detection of an atrial arrhythmia occurs at a later time, such that another high-voltage shock is required as determined at decision step 408, the process begins again by determining if the synchronization criteria are satisfied at the upper ventricular refractory period limit (decision step 410).

In an alternative embodiment, step 440 for resetting the operating refractory period to the upper limit is performed only if VT/VF is detected following the atrial shock. If an atrial therapy is successfully synchronized to a higher ventricular rate, without detection of VT/VF following the atrial shock, the operating refractory period may remain at the adjusted setting for future synchronization attempts.

Figure 4A:
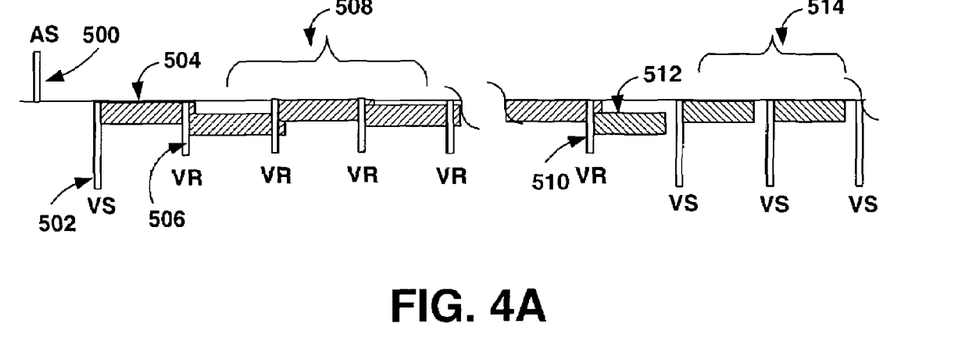
FIG. 4A illustrates time intervals and events associated with an adjustable atrial cardioversion/defibrillation ventricular refractory period provided by the present invention.

FIG. 4A illustrates time intervals and events associated with an adjustable atrial cardioversion/defibrillation synchronization ventricular refractory period provided by the present invention. An atrial sense (AS) event 500 marks the onset of an atrial tachycardia/fibrillation detection episode. The first ventricular sense (VS) event 502 after atrial tachycardia/fibrillation detection is immediately followed by an atrial synchronization ventricular refractory period 504. In accordance with method 400 described above, this refractory period 504 is initially equal to an upper refractory period limit. In this example, the next ventricular event is a ventricular refractory (VR) sense event 506, occurring within the refractory period 504. A series of ventricular refractory sense events 508 are shown following event 506, all of which occur just within the refractory period immediately following the preceding ventricular event. The ventricular rate is seen to be just greater than the rate corresponding to the upper refractory period limit.

Ventricular refractory sense event 510 represents the R-wave sensed after the Nth R-R interval used for determining if the atrial synchronization criteria are met according to the methods described. According to prior art, an atrial therapy would be aborted under these conditions because the synchronization criteria would not be satisfied. However, according to the present invention, if a predetermined number of sensed ventricular events (M) out of a given number of consecutive ventricular events (N) do not fall outside the refractory period, the refractory period is decreased by a predetermined interval to the adjusted refractory period 512. In this example, a subsequent series of ventricular sense events 514 occur outside the adjusted refractory period. Atrial synchronization criteria are likely to be satisfied, allowing a synchronized atrial shock to be delivered.

Figure 4B:
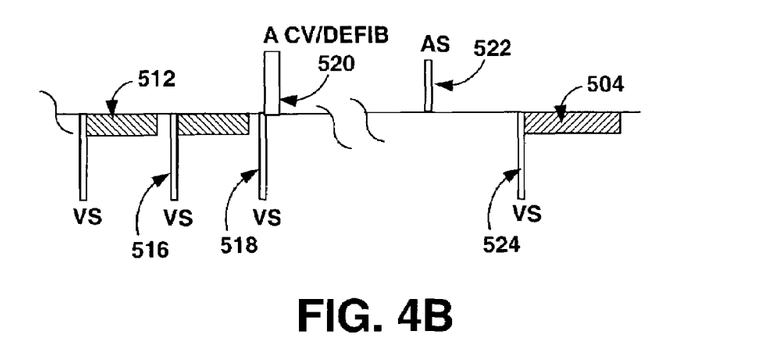
FIG. 4B illustrates the synchronization of an atrial shock to a ventricular event according to the present invention.

FIG. 4B illustrates the synchronization of an atrial shock to a ventricular event according to the present invention. In this example, atrial synchronization criteria are satisfied upon sensing ventricular sense event 516 outside of the adjusted ventricular refractory period 512. Ventricular sense event 516 marks the Mth event but of N consecutively sensed ventricular events to fall outside the adjusted refractory period 512. An atrial shock 520 is therefore synchronized to the next ventricular sense event 518 that occurs outside the adjusted refractory period 512. If detection of the atrial arrhythmia is sustained after shock 520, or if another atrial arrhythmia episode is detected later, beginning with atrial sense event 522, the next ventricular sense event 524 initiates a refractory period 504 that has been reset to the upper refractory period limit.

Figure 4C:
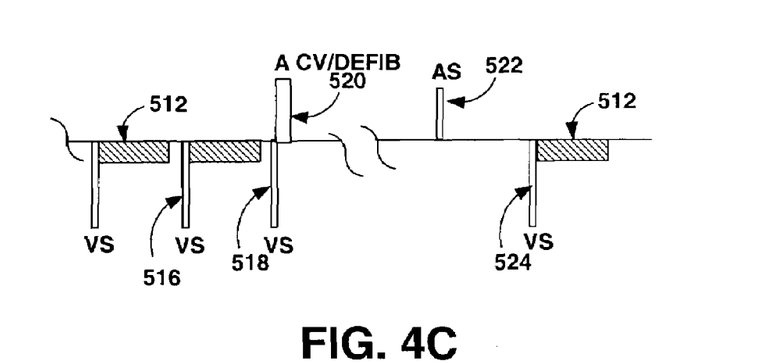
FIG. 4C illustrates an alternative embodiment of the atrial cardioversion/defibrillation synchronization method provided by the present invention.

FIG. 4C illustrates an alternative embodiment of the atrial synchronization method provided by the present invention. Identically labeled elements in FIG. 4C correspond to those in FIG. 4B. In this embodiment, however, the refractory period following a ventricular sense event 524 after an atrial arrhythmia re-detection that begins with atrial sense event 522 remains at the previously adjusted refractory period 512. The atrial shock 510 was safely synchronized to a ventricular sense event 518 without VT/VF detection. However, if VT/VF had been detected following the atrial shock 520, the refractory period would be reset to the upper limit.

Figure 5:
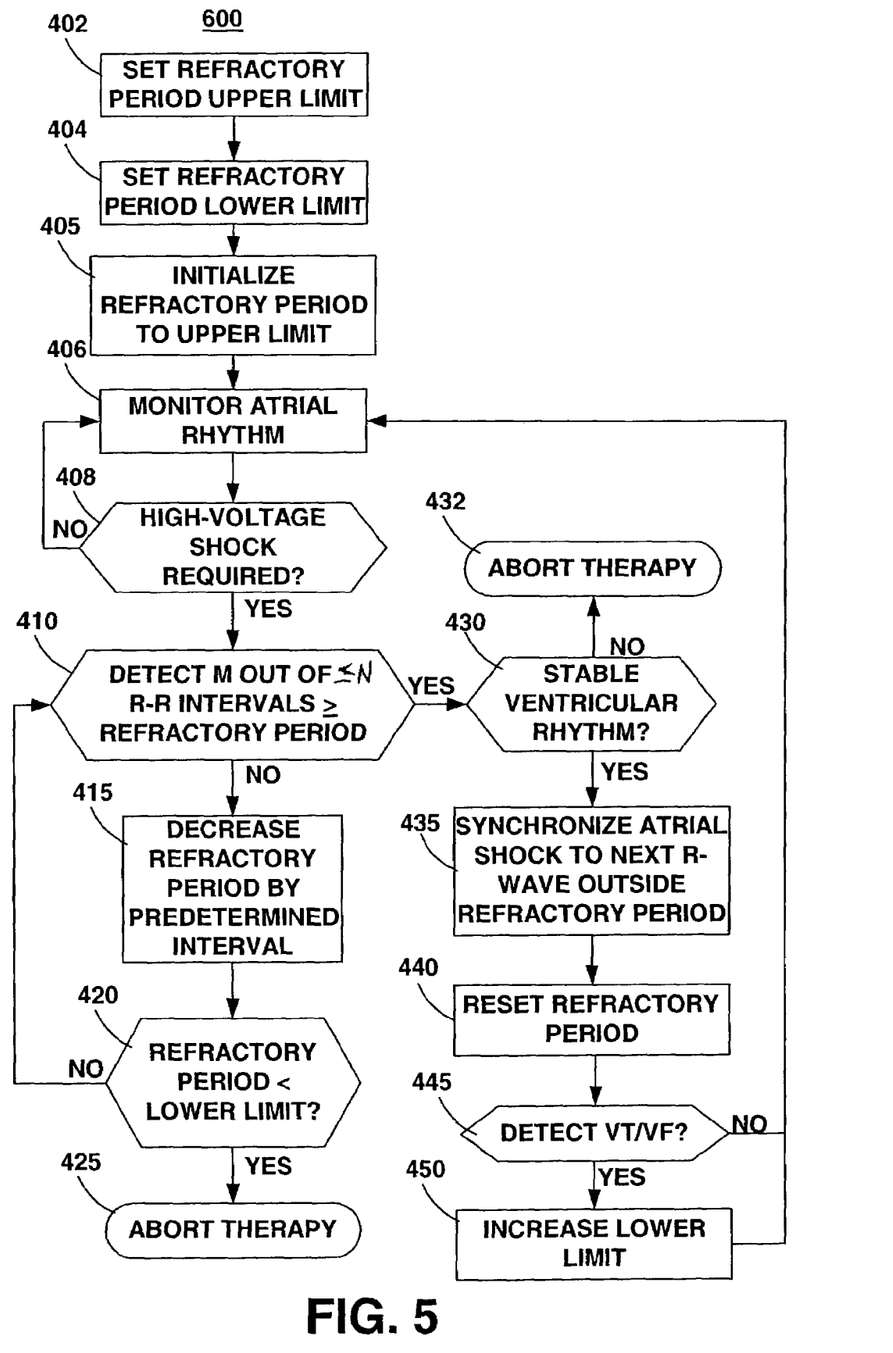
FIG. 5 is a flow chart of an alternative method for controlling the synchronization of an atrial defibrillation or cardioversion shock with a ventricular depolarization, according to the present invention.

FIG. 5 is a flow chart summarizing the steps included in an alternative method for controlling the synchronization of an atrial defibrillation or cardioversion shock with a ventricular depolarization. Identically labeled steps included in method 600 correspond to those in method 400 described above. Method 600, however, includes a step 430 for verifying a stable ventricular rhythm prior to delivering an atrial shock.

Synchronization of an atrial shock to an unstable ventricular rhythm may be proarrhythmic. Therefore, it may be desirable to include additional criteria regarding ventricular rhythm stability that must be satisfied prior to delivering a ventricular synchronized atrial shock. An unstable ventricular rhythm, such as long-short syndrome, may exist that results in satisfaction of the synchronization criteria based on an atrial cardioversion/defibrillation ventricular refractory period but is still regarded as too instable for synchronizing an atrial shock. As such, decision step 430 for verifying ventricular stability may be included in a method for synchronizing an atrial shock to a ventricular depolarization.

In one embodiment, ventricular stability may be determined by measuring the successive differences between a number of consecutive R-R intervals and verifying that these differences do not exceed some predetermined limit or percentage of a reference R-R interval or average R-R interval. In alternative embodiments, ventricular rate stability is verified according to a standard deviation of an average R-R interval that may not exceed a predetermined amount or percentage of the average. It is expected that any method for determining ventricular rate stability known in the art may be usefully practiced with the present invention. For example, ventricular rate stability criteria may be set forth as described in the above-incorporated '186 patent to Olson, or alternatively according to methods described in the above-cited '850 patent issued to Dawson and '438 patent issued to Chen, both of which patents are incorporated herein by reference in their entirety. According to an embodiment of the present invention, an unstable ventricular rate is determined to exist when there is more than a predetermined percentage of cycle length difference between two adjacent intervals that are longer than the operating refractory period. The predetermined difference is programmable, and for example, could be set at 15-20%

If ventricular stability is not verified at step 430, the atrial shock therapy is aborted at termination step 432. If ventricular stability is verified, the scheduled atrial shock is delivered at step 435, synchronized to the next ventricular depolarization outside the current refractory period. In one embodiment, ventricular stability is verified by detecting no more than a given percentage difference, for example 10 to 20% difference, between the ventricular cycle lengths that are longer than the current operating atrial cardioversion/defibrillation ventricular refractory period.

Some of the techniques described above may be embodied as a computer-readable medium comprising instructions for a programmable processor such as microprocessor 224 or pacer timing/control circuitry 212 shown in FIG. 2. The programmable processor may include one or more individual processors, which may act independently or in concert. A "computer-readable medium" includes but is not limited to read-only memory, Flash memory and a magnetic or optical storage medium. The medium includes instructions for causing a processor to perform the method for controlling the synchronization of an atrial defibrillation or cardioversion shock with a ventricular depolarization according to the present invention, as described above.

Thus, an implantable cardioverter defibrillator system and method have been described that allow an atrial cardioversion/defibrillation ventricular refractory period to be automatically adjusted within upper and lower refractory period limits. Atrial cardioversion and defibrillation therapies are thus safely synchronized during ventricular rates that may be relatively higher than what a prior art fixed refractory period would allow. While the present invention has been described according to specific embodiments presented herein, these embodiments are intended to be exemplary, not limiting, with regard to the following claims.

The invention claimed is:

1. A method of controlling a therapy in an implantable medical device, comprising:
   setting a refractory period upper limit;
   setting a lower limit for the refractory period;
   initializing a refractory period to the refractory period upper limit;
   sensing a cardiac signal other than during the refractory period and determining whether to deliver a therapy in response to the cardiac signal;
   determining whether an R-wave synchronization criteria for delivering the therapy are met; and then
   if the R-wave synchronization criteria are met, delivering the therapy and returning to the sensing step; and
   if the R-wave synchronization criteria are not met, automatically adjusting the refractory period to be less than the refractory period upper limit and return to the sensing step;
   determining whether the refractory period, as adjusted, is less than the lower limit;
   terminating the method in response to the refractory period, as adjusted, being less than the lower limit;
   determining, in response to the refractory period, as adjusted, not being less than the lower limit, whether the R-wave synchronization criteria corresponding to the refractory period, as adjusted, are met for a subsequently sensed cardiac signal;
   delivering the therapy in response to the R-wave synchronization criteria being met for the subsequently sensed cardiac signals; and
   automatically adjusting the refractory period, as adjusted, in response to the R-wave synchronization criteria not being met.

2. The method of claim 1, wherein determining whether R-wave synchronization criteria are met further comprises determining whether a predetermined number of intervals corresponding to the cardiac signal are greater than or equal to the refractory period.

3. The method of claim 1, wherein automatically adjusting the refractory period further comprises decreasing the refractory period by a predetermined interval.

4. The method of claim 1, wherein delivering the therapy further comprises synchronizing the delivery of the therapy to a next interval corresponding to the cardiac signal greater than the refractory period.

5. The method of claim 1, wherein the refractory period has an upper limit and a lower limit, and wherein determining whether R-wave synchronization criteria are met comprises determining whether a predetermined number of intervals corresponding to the cardiac signal are within the upper limit and the lower limit.

6. The method of claim 5, wherein the delivered therapy corresponds to an atrial shock therapy.

7. The method of claim 6, further comprising determining whether sensed cardiac signals subsequent to the delivered therapy correspond to ventricular arrhythmia, and resetting the lower limit in response to the cardiac signal subsequent to the delivered therapy corresponding to ventricular arrhythmia.

8. The method of claim 6, further comprising verifying a stable ventricular rhythm prior to delivering the therapy.

9. An implantable medical device, comprising:
   means for setting a refractory period upper limit;
   means for initializing a refractory period to the refractory period upper limit;
   means for sensing cardiac signals other than during the refractory period and determining whether to deliver a therapy in response to the sensed cardiac signals;
   means for determining whether R-wave synchronization criteria for delivering the therapy are met;
   means for delivering the therapy in response to the synchronization criteria being met; and
   means for automatically adjusting the refractory period in response to the synchronization criteria not being met;
   means for setting a lower limit for the refractory period and wherein the determining means determines whether the refractory period, as adjusted, is less than a lower limit, and determines, in response to the refractory period, as adjusted, not being less than the lower limit, whether the synchronization criteria corresponding to the refractory period, as adjusted, are met for subsequently sensed cardiac signals, the delivery means delivers the therapy in response to the synchronization criteria being met for the subsequently sensed cardiac signals, and the adjusting means adjusts the refractory period, as adjusted, in response to the synchronization criteria not being met.

10. The device of claim 9, wherein the determining means determines whether the synchronization criteria corresponding to the refractory period, as adjusted, are met for subsequently sensed cardiac signals, the delivering means delivers the therapy in response to the synchronization criteria being met for the subsequently sensed cardiac signals, and the adjusting means automatically adjusts the refractory period, as adjusted in response to the synchronization criteria not being met.

11. The device of claim 9, wherein the determining means determines whether a predetermined number of intervals corresponding to the sensed cardiac signals are greater than or equal to the refractory period.

12. The device of claim 9, wherein the adjusting means decreases the refractory period by a predetermined interval.

13. The device of claim 9, wherein the delivering means synchronizes the delivery of the therapy to a next interval corresponding to the sensed cardiac signals greater than the refractory period.

14. The device of claim 9, wherein the refractory period has an upper limit and a lower limit, the determining means determines whether a predetermined number of intervals corresponding to the sensed cardiac signals are within the upper limit and the lower limit, and the adjusting means decreases the refractory period.

15. The device of claim 14, wherein the delivered therapy corresponds to an atrial shock therapy.

16. The device of claim 15, further comprising means for determining whether sensed cardiac signals subsequent to the delivered therapy correspond to ventricular arrhythmia, and resetting the lower limit in response to sensed cardiac signals subsequent to the delivered therapy corresponding to ventricular arrhythmia.

17. The device of claim 15, further comprising means for verifying a stable ventricular rhythm prior to delivering the therapy.

* * * * *